United States Patent [19]

Duffett

[11] Patent Number: Plant 5,737

[45] Date of Patent: May 6, 1986

[54] CHRYSANTHEMUM PLANT NAMED THRILL

[75] Inventor: William E. Duffett, Salinas, Calif.

[73] Assignee: Yoder Brothers, Inc., Barberton, Ohio

[21] Appl. No.: 644,262

[22] Filed: Aug. 27, 1984

[51] Int. Cl.[4] ..... A01H 5/00
[52] U.S. Cl. ..... Plt./74
[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Thrill characterized as to uniqueness by the combined characteristics of flat capitulum form, daisy capitulum type, orange red ray floret color, diameter across face of capitulum ranging from 3.5 to 4.5 cm. at maturity, uniform seven to eight week flowering response, medium plant height, spreading, branching pattern, and tolerance of both low winter 13° C. minimum and high summer 24° C. night to 38° C. day temperatures for bud initiation and flower development.

3 Drawing Figures su

The present invention comprises a new and distinct cultivar of *Chrysanthemum morifolium,* Ramat., named Thrill.

Thrill is a product of a planned breeding program which had the objective of creating new chrysanthemum cultivars for pinched spray pot mum programs having daisy capitulum type, orange red floret color, seven to eight week flowering response and the ability to produce commercially acceptable quality in year round programs. Such traits in combination were not present or required improvements in previously available commercial cultivars.

Thrill was originated from a cross made in a controlled breeding program in Salinas, Calif. in 1979. The female parent was an unnamed bronze daisy seedling originated by the present inventor and identified as 781013002. The male parent of Thrill was an unnamed orange daisy spoon seedling originated from a cross between two unnamed seedlings.

Thrill was discovered and selected as one flowering plant within the progeny of the stated cross by William E. Duffett in September 1980 in a controlled environment in Salinas, Calif.

The first act of asexual reproduction of Thrill was accomplished when vegetative cuttings were taken from the initial selection in Nov. 1980 in a controlled environment in Salinas, Calif. by a technician working under formulations established and supervised by William E. Duffett. Horticultural examination of selected units initiated July 15, 1981 has demonstrated that the combination of characteristics as herein disclosed for Thrill are firmly fixed and are retained through successive generations of asexual reproduction.

Thrill has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Thrill which in combination distinguish this chrysanthemum as a new and distinct cultivar:

(1) Flat capitulum form.
(2) Daisy capitulum type.
(3) Orange red ray floret color.
(4) Diameter across face of capitulum ranging from 3.5 to 4.5 cm. at maturity.
(5) Uniform seven to eight week photoperiodic flowering response to short days.
(6) Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots).
(7) Spreading, branching pattern.
(8) Tolerance of low winter 13° C. minimum temperatures.
(9) Tolerance of high summer 24° C. night to 38° C. day temperatures.

The accompanying photographic drawings depict typical leaf and inflorescence characteristics of Thrill. Sheet 1 is a color photograph of a plant of Thrill grown as a pinched spray pot mum, with colors being as accurate as possible with renditions of this type. Sheet 2 is a black and white photograph of three views of the inflorescence of Thrill. Sheet 3 shows the upper and under surfaces of the leaves of Thrill in three stages of growth (mature, intermediate, immature).

Of the many commercial cultivars known to the present inventor, the most similar in comparison to Thrill is Spark, disclosed in U.S. Plant Pat. No. 3,946. Reference is made to attached Chart A which compares certain characteristics of Thrill to those same characteristics of Spark. Traits similar in both cultivars are form, type and response. Thrill has a more spreading plant habit, a smaller inflorescence diameter, more intense orange in ray floret color, and its tolerance of low 13° C. temperatures results in superior high light winter performance.

In the following description, color references are made to The Royal Horticultural Society Colour Chart. The color values were determined between 2:30 P.M. and 2:45 P.M. on March 1, 1984 under 380 foot-candle light intensity at Salinas, Calif.

Classification:
*Botanical.—Chrysanthemum morifolium,* Ramat., cv THRILL.

*Commercial.*—Daisy spray pot mum.

I. INFLORESCENCE

A. Capitulum:
- *Form.*—Flat.
- *Type.*—Daisy.
- *Diameter across face.*—3.5 to 4.5 cm.

B. Corolla of ray florets:
- *Color (general tonality from a distance of three meters).*—Orange red.
- *Color (upper surface).*—46A-B oxidizing to 45A-B.
- *Color (under surface).*—163C streaked with 168B-C.
- *Shape.*—Short, broad, rounded tip.

C. Corolla of disc florets:
- *Color (mature).*—6C.
- *Color (immature).*—149A.

D. Reproductive organs:
- *Androecium.*—Present disc florets only; scant pollen.
- *Gynoecium.*—Present both ray and disc florets.

II. PLANT

A. General appearance:
- *Height.*—Medium.
- *Branching pattern.*—Spreading.

B. Foliage:
- *Color (upper surface).*—137A-B.
- *Color (under surface).*—138B.
- *Shape.*—Shallow lobed. Blunt edging with moderate serration.

CHART A

COMPARISON OF THRILL AND SPARK

| CULTI- | RAY FLORET | CAPITULUM | BRANCHING |
|---|---|---|---|

CHART A-continued

COMPARISON OF THRILL AND SPARK

| VAR | COLOR | FORM AND TYPE | PATTERN |
|---|---|---|---|
| THRILL | ORANGE RED | FLAT DAISY | SPREADING |
| SPARK | RED | FLAT DAISY | SEMI-SPREADING |

| CULTI-VAR | DIAMETER ACROSS FACE OF CAPITULUM | PLANT HEIGHT | FLOWERING RESPONSE PERIOD | TEMPERATURE TOLERANCE |
|---|---|---|---|---|
| THRILL | 3.5 to 4.5 cm. | MEDIUM | SEVEN TO EIGHT WEEKS | LOW - 13° C. HIGH - 24° C. Night to 38° C. Day |
| SPARK | 3.5 to 5.5 cm. | SHORT | SEVEN WEEKS | LOW - POOR HIGH - 24° C. Night to 38° C. Day |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Thrill, as described and illustrated, and particularly characterized as to uniqueness by the combined characteristics of flat capitulum form; daisy capitulum type; orange red ray floret color; diameter across face of capitulum ranging from 3.5 to 4.5 cm. at maturity; uniform seven to eight week flowering response; medium plant height; spreading, branching pattern, and tolerance of both low winter 13° C. minimum and high summer 24° C. night to 38° C. day temperatures for bud initiation and flower development.

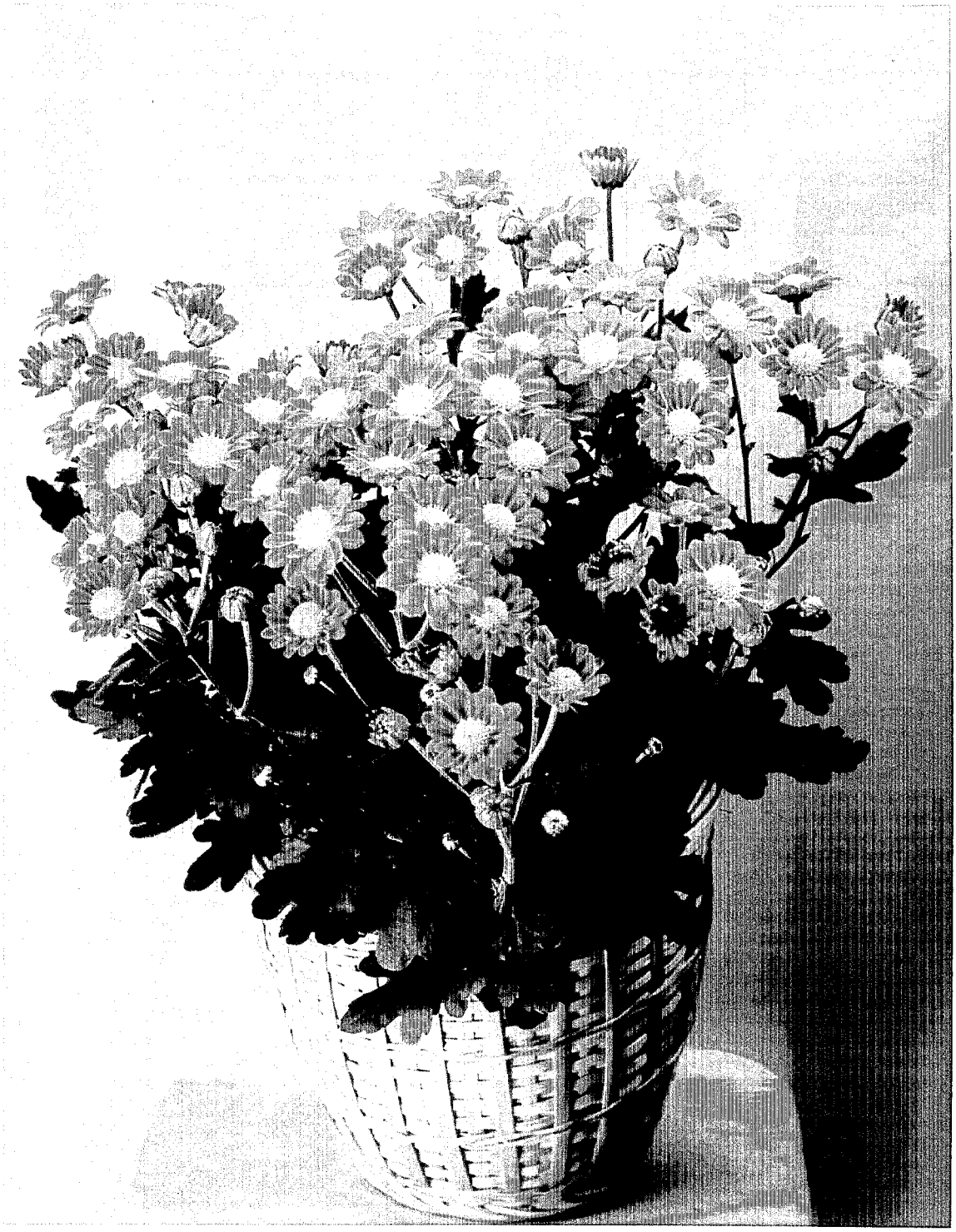

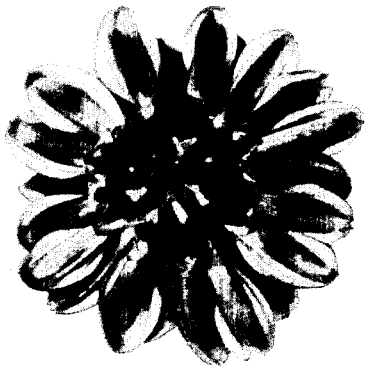
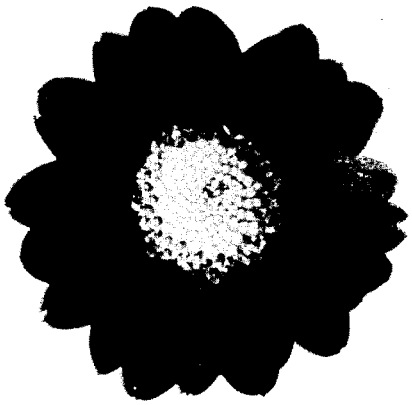
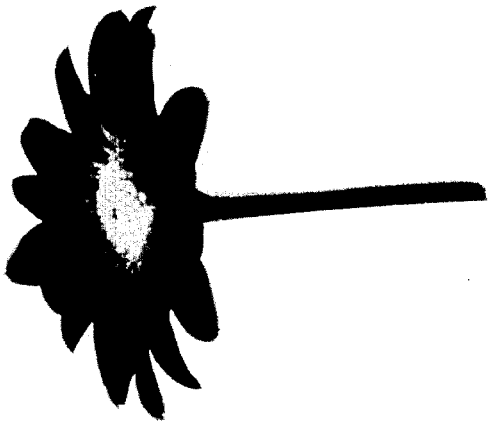

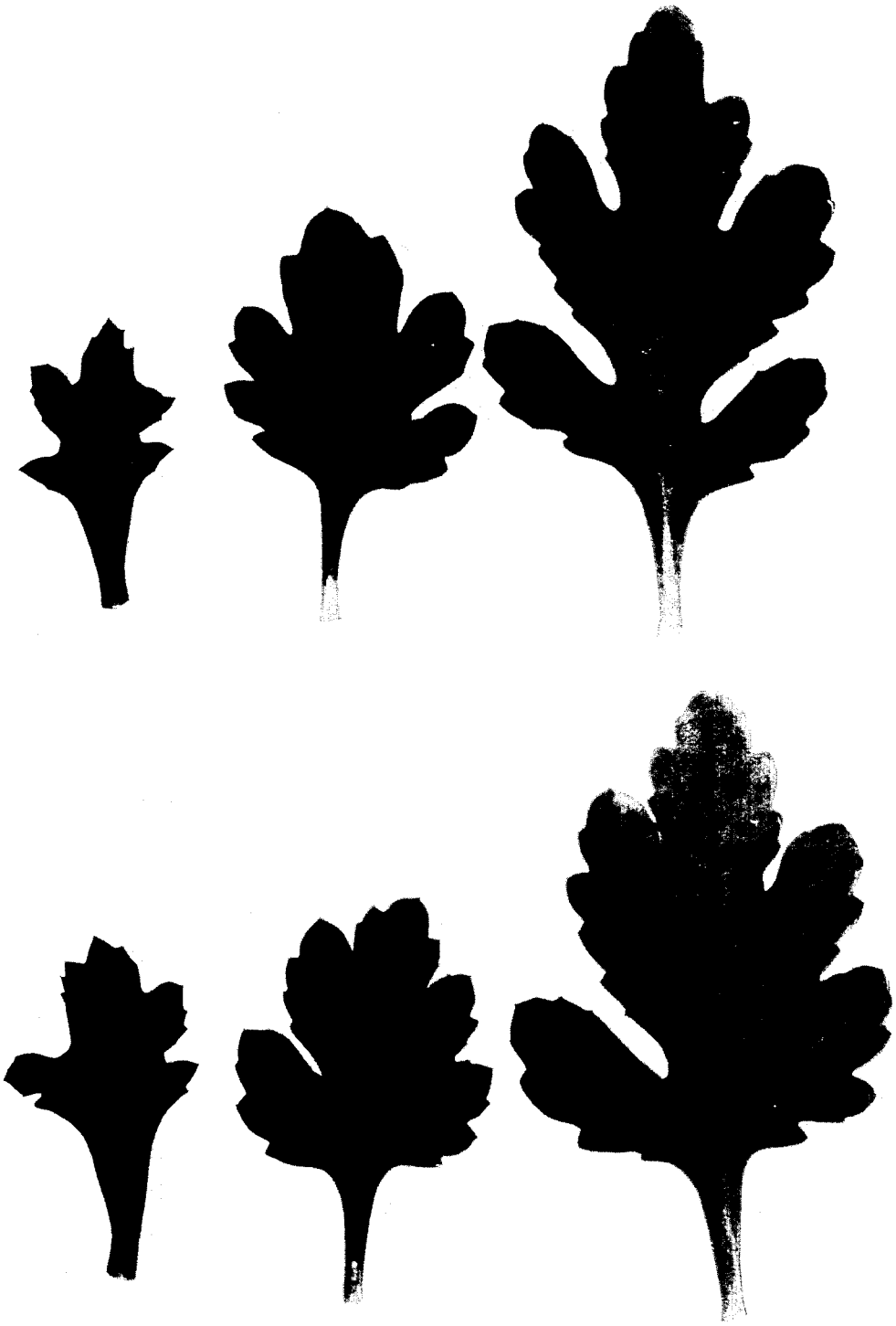

* * * * *